United States Patent
Shim et al.

(10) Patent No.: US 9,068,914 B2
(45) Date of Patent: Jun. 30, 2015

(54) NANOGAP SENSOR AND METHOD OF MANUFACTURING THE SAME

(75) Inventors: Jeo-young Shim, Yongin-si (KR); Tae-han Jeon, Hwaseong-si (KR); Kun-sun Eom, Seoul (KR); Dong-ho Lee, Seongnam-si (KR); Hee-jeong Jeong, Seoul (KR); Seong-ho Cho, Gwacheon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 188 days.

(21) Appl. No.: 13/605,711

(22) Filed: Sep. 6, 2012

(65) Prior Publication Data

US 2013/0265031 A1     Oct. 10, 2013

(30) Foreign Application Priority Data

Apr. 5, 2012 (KR) .................... 10-2012-0035600

(51) Int. Cl.
| | |
|---|---|
| *G01N 27/414* | (2006.01) |
| *G01N 15/10* | (2006.01) |
| *B82Y 15/00* | (2011.01) |
| *G01N 33/487* | (2006.01) |
| *G01N 15/00* | (2006.01) |

(52) U.S. Cl.
CPC ............ *G01N 15/1031* (2013.01); *B82Y 15/00* (2013.01); *G01N 33/48721* (2013.01); *G01N 15/1056* (2013.01); *G01N 2015/0038* (2013.01)

(58) Field of Classification Search
CPC ........ G01N 27/414; G01K 7/01; G01K 15/00
USPC ......... 324/717, 715, 713, 693, 692, 691, 663, 324/658, 649, 71.7, 71.5, 76.11; 977/852, 977/953; 204/403.01
See application file for complete search history.

(56) References Cited

U.S. PATENT DOCUMENTS

| | | | |
|---|---|---|---|
| 6,905,586 B2 | 6/2005 | Lee et al. | |
| 7,144,486 B1 * | 12/2006 | Fritsch et al. | ............ 204/403.06 |
| 7,258,838 B2 | 8/2007 | Li et al. | |
| 7,312,096 B2 | 12/2007 | Kurtz | |
| 7,582,490 B2 | 9/2009 | Golovchenko et al. | |
| 7,638,034 B2 | 12/2009 | Sansinena et al. | |
| 7,857,963 B2 * | 12/2010 | Sasaki et al. | .................. 205/775 |
| 8,044,472 B2 | 10/2011 | Kurtz et al. | |
| 2007/0034975 A1 | 2/2007 | Kurtz | |

(Continued)

OTHER PUBLICATIONS

Tsutsui et al., "Single-molecule sensing electrode embedded in-plane nanopore," *Scientific Reports*, 1:46; DOI:10.1038/srep00046, pp. 1-6 (2011).

(Continued)

*Primary Examiner* — Arleen M Vazquez
*Assistant Examiner* — Dominic Hawkins
(74) *Attorney, Agent, or Firm* — Leydig, Voit & Mayer, Ltd.

(57) ABSTRACT

A nanogap sensor includes a first layer in which a micropore is formed; a graphene sheet disposed on the first layer and including a nanoelectrode region in which a nanogap is formed, the nanogap aligned with the micropore; a first electrode formed on the grapheme sheet; and a second electrode formed on the graphene sheet, wherein the first electrode and the second electrode are connected to respective ends of the nanoelectrode region.

22 Claims, 10 Drawing Sheets

(56) References Cited

U.S. PATENT DOCUMENTS

| | | |
|---|---|---|
| 2008/0021290 A1* | 1/2008 | Sawa et al. .................... 600/300 |
| 2008/0092502 A1* | 4/2008 | Ando et al. ...................... 55/523 |
| 2009/0283412 A1 | 11/2009 | Sansinena et al. |
| 2010/0327847 A1* | 12/2010 | Leiber et al. ................. 324/71.1 |
| 2011/0024302 A1* | 2/2011 | Li et al. ......................... 205/183 |
| 2011/0056845 A1 | 3/2011 | Stellacci et al. |
| 2011/0068320 A1* | 3/2011 | Marinero et al. ................. 257/9 |
| 2011/0168562 A1* | 7/2011 | Nuckolls et al. ............. 204/600 |
| 2011/0197657 A1* | 8/2011 | Gole ............................ 73/31.05 |
| 2012/0037919 A1* | 2/2012 | Xu et al. ......................... 257/76 |
| 2012/0132893 A1* | 5/2012 | Heo et al. ........................ 257/29 |
| 2012/0141799 A1* | 6/2012 | Kub et al. ..................... 428/408 |
| 2012/0302454 A1* | 11/2012 | Esfandyarpour ................. 506/9 |
| 2013/0043131 A1* | 2/2013 | Balagurusamy et al. ..... 204/452 |
| 2013/0153855 A1* | 6/2013 | Afzali-Ardakani et al. ....... 257/9 |

OTHER PUBLICATIONS

Ivanov et al, "DNA Tunneling Detector Embedded in a Nanopore," *Nano Letters*, DOI: 10.1021/nl103873a, pp. A-G (2010).

* cited by examiner ions and methods of manufacturing the same.

NANOGAP SENSOR AND METHOD OF MANUFACTURING THE SAME

CROSS-REFERENCE TO RELATED APPLICATIONS

This application claims the benefit of Korean Patent Application No. 10-2012-0035600, filed on Apr. 5, 2012, in the Korean Intellectual Property Office, the disclosure of which is incorporated by reference herein in its entirety.

BACKGROUND

1. Field

The present disclosure relates to nanogap sensors and methods of manufacturing the same.

2. Description of the Related Art

Various methods of detecting target biomolecules, such as a deoxyribonucleic acid (DNA), from a sample have been developed. One such method uses a bio-pore imitation system that has been spotlighted as a high-sensitivity DNA detecting system. Other DNA detecting systems use a nanogap to detect a tunneling current that is generated when DNA or ribonucleic acid (RNA) passes through the nanogap.

However, forming a nanoelectrode having a nanogap is difficult. Metal is usually used in the nanoprocess, often requiring a thickness of several tens of nm (nanometers) or more. As a result, the size of a nanogap formed in the metal layer is typically much larger than the size of target biomolecules, causing resolution of the system to be low.

SUMMARY

The disclosure provides nanogap sensors that may be easily manufactured by using graphene, and methods of manufacturing and using the same.

Additional aspects will be set forth in part in the description which follows and, in part, will be apparent from the description, or may be learned by practice of the presented embodiments.

According to an aspect of the disclosure, a nanogap sensor includes: a micropore layer comprising a micropore; a graphene sheet disposed on the micropore layer and including a nanoelectrode region comprising a nanogap aligned with the micropore; and a first electrode and a second electrode on the graphene sheet and connected to the nanoelectrode region at opposite ends of the nanoelectrode region relative to the nanogap.

A region of the graphene sheet other than the nanoelectrode region may be an inactive region (e.g., a region that has been electrically inactivated). For instance, the surface of the inactive region may be a fluorine (F)-treated, chlorine (Cl)-treated, or bromine (Br)-treated surface.

The micropore layer may include silicon nitride or silicon oxide.

A width of the graphene sheet may be about 100 μm or less.

A width of the nanoelectrode region may be about 100 nm or less.

A diameter of the micropore may be larger than a diameter of the nanogap, a diameter of the micropore may be about 100 μm or less, and a diameter of the nanogap may be about 50 nm or less.

The nanogap sensor may further include a substrate in which an opening is formed, defining a passageway from a top surface of the substrate to a bottom surface of the substrate. The micropore layer may be formed on the top surface of the substrate, and the micropore of the micropore layer may be aligned with the opening.

A side of the opening may include an inclined side, such that the width (diameter) of the opening decreases from a bottom surface of the substrate towards a top surface of the substrate on which the micropore layer is disposed. In other-words, the opening may be tapered and narrowing, wherein the diameter of the opening at the bottom surface of the substrate is larger than the diameter of the opening at the top surface of the substrate.

The nanogap sensor may part of a device that further includes: a water tank in which a sample is contained or accommodated, wherein the sample includes a biomolecule that can pass through the nanogap of the nanogap sensor; and a power supply unit configured to provide an electric field to the sample in the water tank causing the biomolecules in the sample to move.

The nanogap sensor may be positioned in the water tank such that the water tank comprises an upper region and lower region relative to the nanogap sensor.

The power supply unit may include a third electrode and a fourth electrode, which are disposed in upper and lower regions of the water tank, respectively.

The water tank may be filled with water or an electrolyte solution.

According to another aspect of the disclosure, a method of manufacturing a nanogap sensor includes: forming a micropore layer on a substrate, wherein the micropore layer comprises an insulating material; forming a nanoelectrode on the micropore layer, wherein the nanoelectrode comprises graphene; forming a micropore in the micropore layer, wherein the micropore perforates the micropore layer; and forming a nanogap in the nanoelectrode, wherein the nanogap perforates the nanoelectrode and is aligned with the micropore.

In one aspect of the disclosure, forming the nanoelectrode may include: forming a graphene sheet on the micropore layer; and electrically inactivating a portion of the graphene sheet.

In one aspect of the disclosure, electrically inactivating a portion of the graphene sheet may include: forming a metal layer on the graphene sheet; patterning the metal layer in a shape of a structure including nanoregion and a first electrode and a second electrode connected to respective ends of the predetermined nanoregion, to expose a portion of the graphene sheet; treating a surface of the portion of the graphene sheet with fluorine (F), chlorine (Cl), or bromine (Br); and etching a portion of the nanoregion of the metal layer.

Electron beam lithography may be used in patterning the metal layer.

The method may further include, before the etching of the portion of the nanoregion of the metal layer, forming a first electrode pad and a second electrode pad connected to the first electrode and the second electrode, respectively.

A photolithography process may be used in forming the first electrode pad and the second electrode pad.

The nanogap may be formed using a transmission electron microscope (TEM).

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
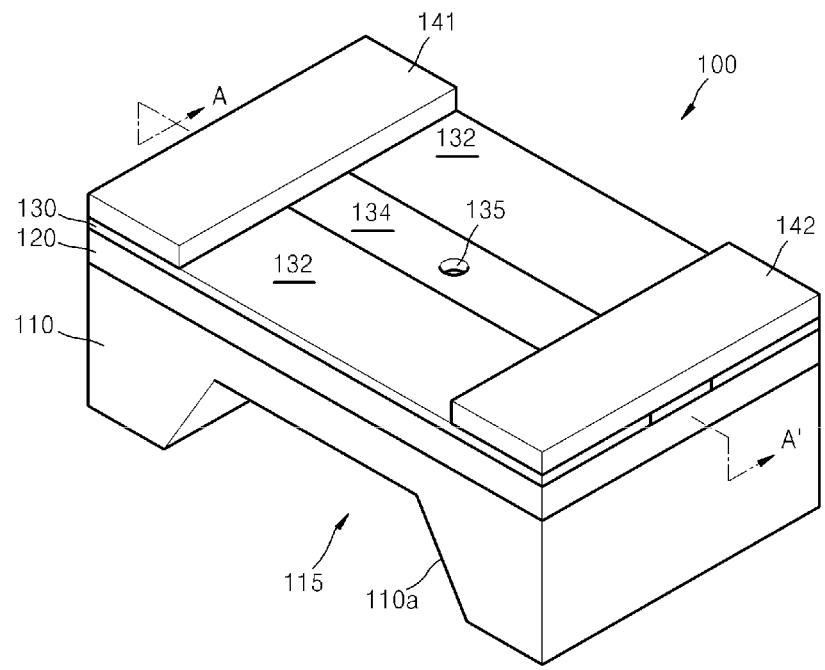
FIG. 1 is a perspective view of a schematic structure of a nanogap sensor according to an embodiment of the disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Figure 2:
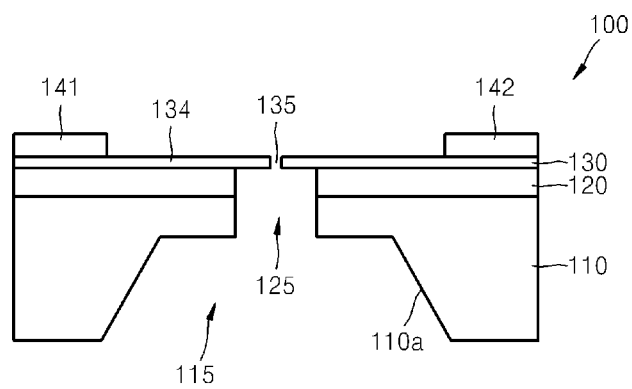
FIG. 2 is a cross-sectional view of the nanogap sensor illustrated in FIG. 1, taken along a line A-A'.

FIG. 1 is a perspective view of a schematic structure of a nanogap sensor 100 according to an embodiment of the disclosure, and FIG. 2 is a cross-sectional view of the nanogap sensor 100 illustrated in FIG. 1, taken along a line A-A'.

Referring to FIGS. 1 and 2, the nanogap sensor 100 includes a micropore layer 120 in which a micropore 125 is formed, and a graphene sheet 130 disposed on the micropore layer 120 and including a nanoelectrode region 134 in which a nanogap 135 is formed in a position in which the nanogap 135 faces the micropore 125.

The graphene sheet 130 further includes an inactive region 132 that is electrically inactivated, as well as the nanoelectrode region 134. The surface of the inactive region 132 is treated with fluorine (F), chlorine (Cl), or bromine (Br), for example. The graphene sheet 130 is a hexagonal single-layer structure formed of, for example, carbon. Since the mobility of charges in the graphene sheet 130 is very high, the graphene sheet 130 functions in the same way as metal having very high electric conductivity. In one embodiment, the region of the graphene sheet 130 that includes the nanoelectrode region 134 has high electric conductivity as its original nature, and the inactive region 132 is partially or completely electrically inactivated. The graphene sheet 130 having the above structure may have any suitable size, and may have a size larger than a nanosize in a physical aspect, but may have an electrical aspect (electrically conductive aspect) of nanosize proportions, for instance, when a nano-sized electrode is formed in order to measure a change in a tunneling current due to target biomolecules that pass through the nanogap 135. For example, the graphene sheet 130 having high conductivity is formed to have the size of several microns, and a portion (e.g., nanosized portion) of the graphene sheet 130, is electrically inactivated. Thus, the graphene sheet comprises a region outside than the nanoelectrode region 134 that is electrically inactivated, and an electrically conductive region that provides a nanoelectrode for measuring a tunneling current as a biomolecule passes through the nanogap in the nanoelectrode.

In one example, the width of the graphene sheet 130 may be about 100 μm (micrometers) or more, or about 1000 μm or more, and the nanoelectrode region 134 of the graphene sheet 130 may have a width of about 100 nm or less, or about 50 nm~100 nm. The length of the nanoelectrode region can be greater than the width, and should be sufficient to accommodate first and second electrodes, each positioned on an end of the lengthwise dimension of the nanoelectrode region. The remaining portion of the graphene sheet, e.g., the regions flanking or surrounding the nanoelectrode region, may constitute the electrically inactivated region.

A more detailed structure and material of the nanogap sensor 100 will now be described below.

A substrate 110 may support the micropore layer 120 and the graphene sheet 130, and may comprise a semiconductor material, a polymer material, or the like. The semiconductor material may include, for example, silicon (Si), germanium (Ge), gallium arsenide (GaAs), gallium nitride (GaN), or the like, and the polymer material may include an organic polymer and an inorganic polymer. The substrate 110 may comprise quartz, glass, or the like, instead of or in addition to the semiconductor material or the polymer material. An opening 115 may be formed in the substrate 110 to have a size (diameter) of several μm or less (e.g., about 10 μm or less, about 5 μm or less, about 1 μm or less, etc.). The opening forms a passage from a bottom surface of the substrate to a top surface of the substrate, and the opening may be tapered, within an opening on the top surface (adjacent the micropore layer) that is smaller in diameter than the opening on the bottom surface. A side wall 110a of the opening 115 may be inclined or angled, such that the width of the opening 115 decreases from a bottom surface of the substrate 110 towards a top surface of the substrate 110 on which the micropore layer 120 is disposed. The opening 115 having such a tapered shape may guide the target biomolecules to easily flow into the micropore 125 from the bottom surface of the substrate 110.

The micropore layer 120 may be formed of an insulating material, for example, a silicon nitride or a silicon oxide. The micropore 125 formed in the micropore layer 120 may be aligned with and connected (fluidly connected) to the opening 115 of the substrate 110. That is, the micropore 125 may be disposed in a position of the micropore layer overlaying or corresponding to the opening 115 in the substrate. The size of the micropore 125 may be determined in consideration of the size of the target biomolecules to be detected. The diameter of the micropore 125 may be larger than the diameter of the nanogap 135 and may be, for example, about 100 μm or less, or about 1 um or less, or about 500 nm~1 μm. The micropore 125 may be formed by any suitable technique, such as by using a focused ion beam (FIB).

The nanogap 135 may be formed on the nanoelectrode region 134 of the graphene sheet 130 and may have a diameter smaller than the micropore, for example, about 50 nm or less or about 5 nm or less. The shape of the nanogap 135 is not limited to the shape illustrated in FIG. 1, and the nanogap 135 may have, for example, a circular shape, an oval shape, or a polygonal shape, among others. Similarly, the shape of the micropore and the opening in the substrate are not limited, and can be, for example, a circular, oval, or polygonal shape, among others.

In addition, a first electrode 141 and a second electrode 142 are formed on the graphene sheet 130. The first electrode 141 and the second electrode 142 may be connected to both ends of the nanoelectrode region 134, respectively. The first electrode 141 and the second electrode 142 may be formed of a conductive material, for example, gold (Au), copper (Cu), silver (Ag), or aluminum (Al).

Figure 3:
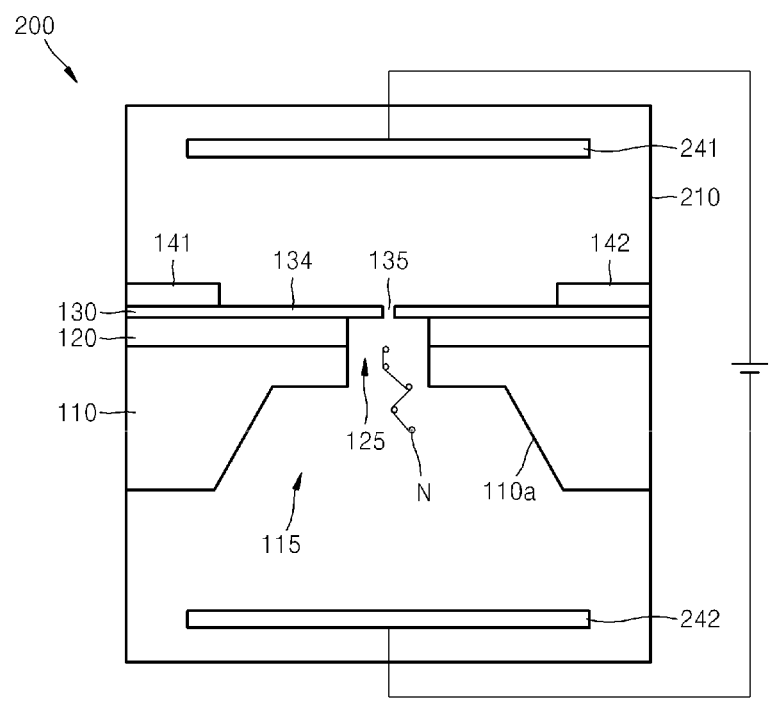
FIG. 3 is a cross-sectional view of a schematic structure of a nanogap sensor according to another embodiment of the disclosure.

FIG. 3 is a cross-sectional view of a schematic structure of a nanogap sensor 200 according to another embodiment of the disclosure.

Referring to FIG. 3, the nanogap sensor can be part of a device 200 in which the nanogap sensor 100 illustrated in FIG. 1 is disposed in a water tank 210 that accommodates a sample to be contacted with or passed through the nanogap 135. The water tank can be, for instance, a channel structure in which target biomolecules in the sample flow and pass through the nanogap sensor.

The nanogap sensor (e.g., a structure including the substrate 110, the micropore layer 120, the graphene sheet 130 including the nanoelectrode region 134 in which the nanogap 135 is formed, and the first electrode 141 and the second electrode 142 disposed on both ends of the nanoelectrode region 134, respectively,) is disposed in the water tank 210. In addition, the device 200 further includes a power supply unit that is configured to provide an electric field to the water tank and the sample contained therein in order to move the target biomolecules in the sample towards and through the nanogap sensor. The nanogap sensor can be positioned in the water tank such that the water tank has an upper and lower region relative to the nanogap sensor. In other words, the nanogap sensor can divide the water tank into an upper and lower regions. The power supply unit includes a third electrode 241 and a fourth electrode 242, which are disposed in upper and lower regions of the nanogap 135, respectively. The water tank 210 may be filled with a buffer solution, such as, for example, water, deionized water, or an electrolyte solution. The buffer solution may be a movement medium for the target biomolecules to be detected by the nanogap sensor 200. When a voltage is applied to the third and fourth electrodes 241 and 242 from an external power source, charged biomolecules in the sample will migrate from one region of the water tank to the other, passing through the nanogap sensor. Since, for example, single strand DNA N has a negative charge, the single strand DNA N may move from the lower region of the nanogap 135 in which the fourth electrode 242 having negative charges is disposed, to the upper region of the nanogap 135 in which the third electrode 241 having positive charges is disposed, due to the electric field generated by the voltage applied to the third and fourth electrodes 241 and 242. That is, the single strand DNA N that flows into the lower region of the nanogap 135 moves to the vicinity of the opening 115 of the substrate 110 due to the electric field and is guided by the opening 115 to be close to the micropore 125. When the single strand DNA N passes through the nanogap 135 after passing through the micropore 125, a base of the single strand DNA N may be classified by measuring a change in electric signal between the first electrode 141 and the second electrode 142, for example, a change in tunneling currents. That is, a change in tunneling currents through the nanogap 135 at an instant of time during which a base of the single strand DNA N passes through the nanogap 135 is measured such that the base may be classified.

Various channel structures that allow target biomolecules to pass through the nanogap 135 and to flow in the sample may be used.

The nanogap sensor 100 and device 200 having the structures illustrated in FIGS. 1-3, respectively, form the nanogap 135 by using the graphene sheet 130 having a thickness of several Å (angstroms), for example, about 15 Å or less, or about 4 Å or less so that the resolution for detecting the target biomolecules passing through the nanogap 135 may be improved.

FIGS. 4A through 4L are cross-sectional views illustrating a method of manufacturing a nanogap sensor, according to an embodiment of the disclosure.

Figure 4A:
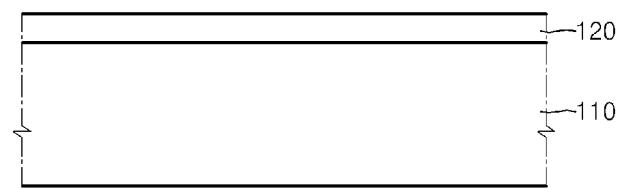
FIGS. 4A through 4L are cross-sectional views illustrating a method of manufacturing a nanogap sensor, according to one embodiment of the disclosure.

First, as illustrated in FIG. 4A, a micropore layer 120 is formed on a substrate 110 by using an insulating material. A material used in forming the micropore layer 120 may be, for example, a silicon oxide or a silicon nitride. The substrate 110 may be a semiconductor substrate or a polymer substrate formed of various materials. For example, the substrate 110 may be prepared by polishing a silicon substrate to have a predetermined thickness of about 300 µm by using a method, such as chemical mechanical polishing (CMP). Although not shown, on a bottom surface of the substrate 110, an etch mask layer for forming a predetermined opening may be further disposed.

Figure 4B:
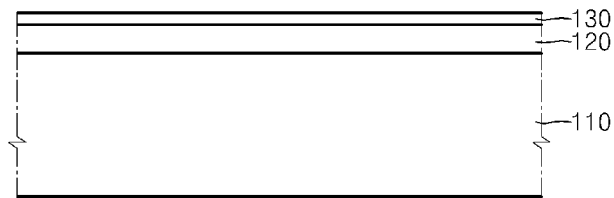

Referring to FIG. 4B, a graphene sheet 130 is formed on the micropore layer 120. The graphene sheet 130 may be transferred onto the substrate 110.

Figure 4C:
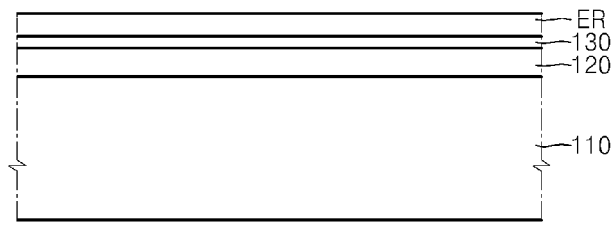

Next, as illustrated in FIG. 4C, an electron beam resist ER is formed on the graphene sheet 130. The electron beam resist ER is hardened by an electron beam and has relatively high resolution of, for example, about 50 nm, when compared to a general photoresist, and thus, by using the electron beam resist ER nano-patterning is possible.

Figure 4D:
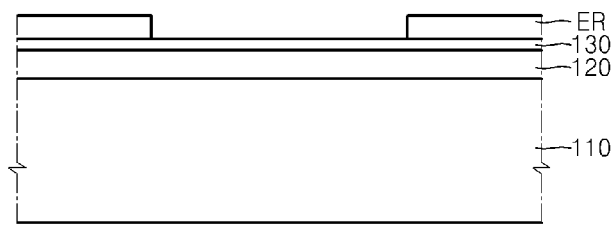
Figure 4E:
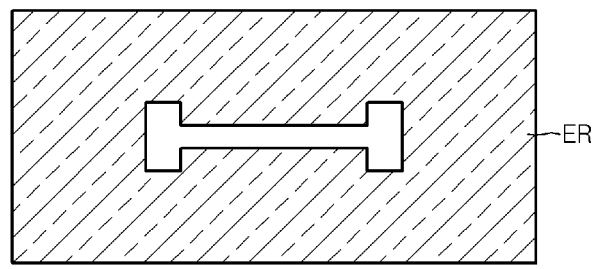

Referring to FIG. 4D and FIG. 4E, which is a plan view of FIG. 4D, the electron beam resist ER is patterned so that a portion of the graphene sheet 130 including a predetermined nanoregion may be exposed. For example, the exposed nanoregion of the graphene sheet 130 is a region that corresponds to the nanoelectrode region of the nanogap sensor, and a region that corresponds to first and second electrodes to be formed on both ends of the nanoelectrode region, as illustrated in FIGS. 4D and 4E. By way of further illustration, the nanoregion can have a width of about 100 nm or less, and a length longer than its width. The nanoregion can have a length sufficient to accommodate the first and second electrodes connected to opposite ends of the nanoregion of exposed grapheme relative to a nanogap formed in the graphene layer.

Figure 4F:
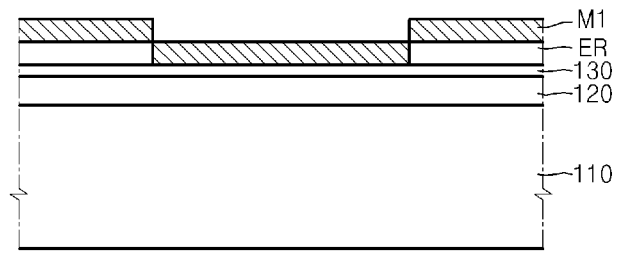

Next, as illustrated in FIG. 4F, a first metal layer M1 is formed above the electron beam resist ER and the graphene sheet 130. The first metal layer M1 may be formed of material having high electric conductivity, such as, for example, Au, Cu, Ag, or Al. Next, when the electron beam resist ER is removed by performing a lift off process, a portion of the first metal layer M1 formed above the electron beam resist ER is removed together with the electron beam resist ER.

Figure 4G:
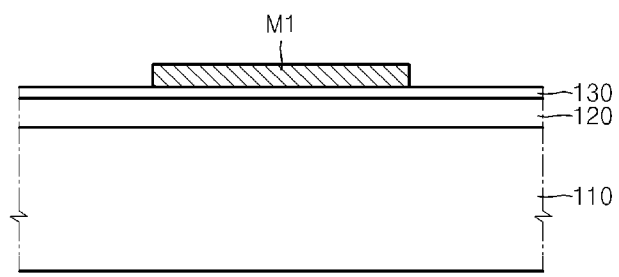
Figure 4H:
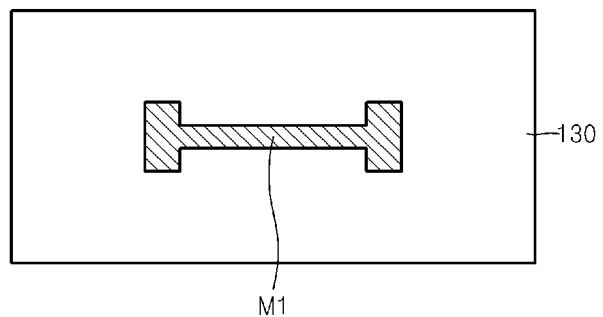

FIGS. 4G and 4H are a cross-sectional view and a plan view, respectively, illustrating a result of performing the lift off process in FIG. 4F. A shape of the pattered first metal layer M1 is reverse to a shape of the patterned electron beam resist ER of FIG. 4E, and a region of the graphene sheet 130 corresponding to the patterned first metal layer M1 is a region to be protected in a subsequent inactivation process.

Figure 4I:
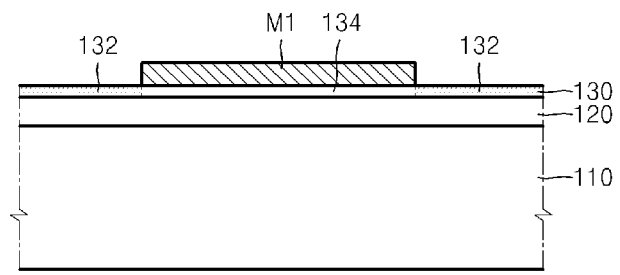

FIG. 4I illustrates an inactivation process in which the exposed portion of the graphene sheet 130 is electrically inactivated. For example, when surface treatment is performed using gas generated by combining $XeF_2:N_2$ at a ratio of 1:35 and brief annealing is performed at 150° C., the surface of the graphene sheet 130 is combined with F. In this way, a region of the graphene sheet 130 that is fluorinated is an inactive region 132 that is electrically inactivated. That is, the region of the graphene sheet 130 that is shielded by the first metal layer M1 has its original electric characteristic, and the remaining region of the graphene sheet 130 is the inactive region 132. In other examples, the inactivation process may be performed using Br or Cl, instead of F.

Figure 4J:
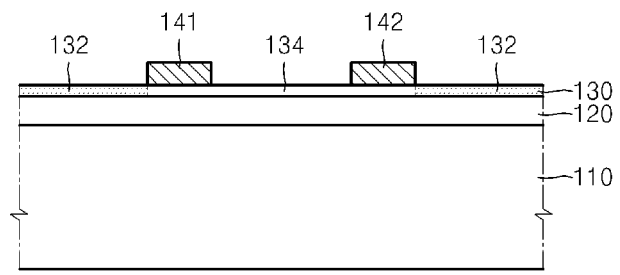

Next, as illustrated in FIG. 4J, when a portion of the patterned first metal layer M1 is removed by etching in order to expose the nanoelectrode region 134 of the graphene sheet 130, the first electrode 141 and the second electrode 142 are formed on the graphene sheet 130.

By performing the above process, the region of the graphene sheet 130 includes the nanoelectrode region 134 having its original electric characteristic and the inactive region 132 in the vicinity of the nanoelectrode region 134.

Figure 4K:
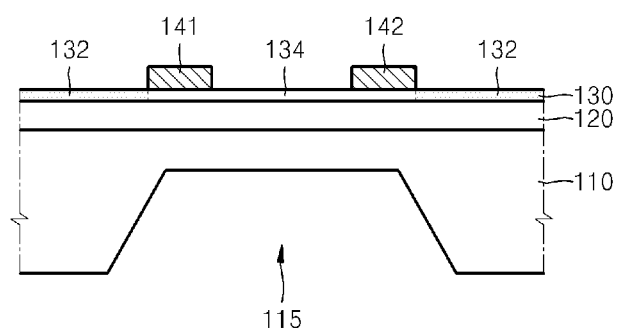
Figure 4L:
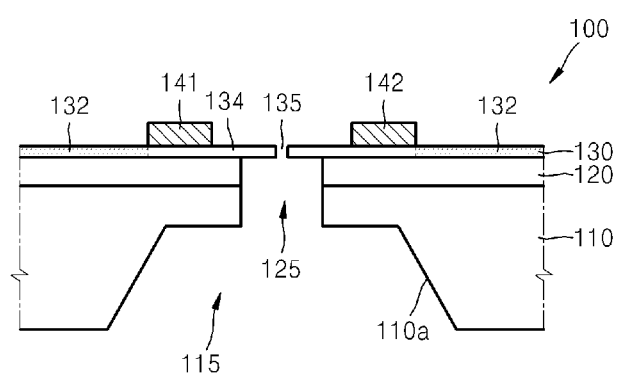

Next, FIGS. 4K and 4L illustrate a process of forming an opening 115 (i.e., FIG. 4K) and a micropore 125 and a nanogap 135 (i.e., FIG. 4L). Referring to FIGS. 4K and 4L, after an opening 115 is formed in a bottom surface of the substrate 110 by using a method, such as etching or the like, the micropore 125 and the nanogap 135 are formed such that the nanogap sensor 100 is formed. The micropore 125 may be formed in a position in which the micropore 125 is connected to the opening 115, by using FIB equipment. In addition, the nanogap 135 may be formed in a position in which the nanogap 135 is connected to the micropore 125, by using transmission electron microscope (TEM) equipment. The micropore 125 may have a larger diameter than that of the nanogap 135 that is, for example, about 100 μm or less, and the nanogap 135 may have a diameter of, for example, about 50 nm or less. The shape of the nanogap 135 is not limited thereto, and the nanogap 135 may have, for example, a circular shape, an oval shape, or a polygonal shape.

FIGS. 5A through 5F are cross-sectional views illustrating a method of manufacturing a nanogap sensor, according to another embodiment of the disclosure.

The method of manufacturing a nanogap sensor illustrated in FIGS. 5A through 5F is different from the method of manufacturing a nanogap sensor illustrated in FIGS. 4A through 4L in that a process of forming an electrode pad is additionally performed before the first metal layer M1 is etched so that the nanoelectrode region 134 of the graphene sheet 130 may be exposed after the inactivation process of FIG. 4I has been performed.

Figure 5A:
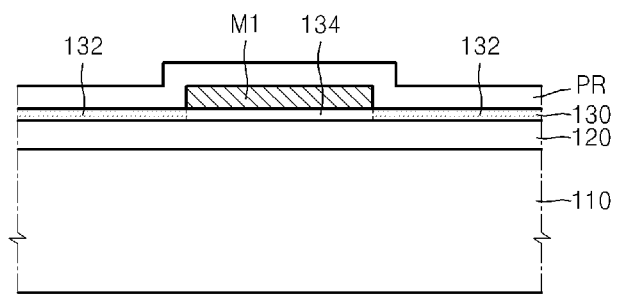
FIGS. 5A through 5H are cross-sectional views illustrating a method of manufacturing a nanogap sensor, according to another embodiment of the disclosure.

Referring to FIG. 5A, after the inactivation process of FIG. 4I has been performed, a photoresist PR is patterned in the shape of an electrode pad to be formed. In this case, a general photolithography process may be performed, for example.

Figure 5B:
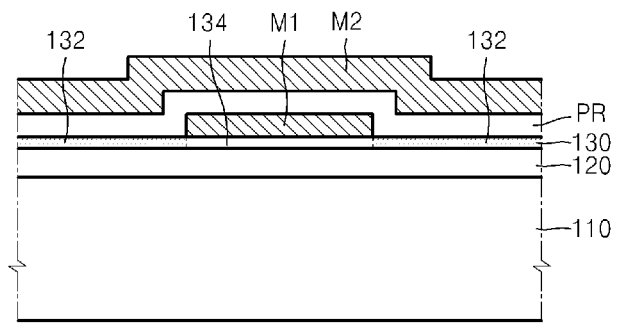

Next, as illustrated in FIG. 5B, when a second metal layer M2 is formed on the photoresist PR and the graphene sheet 130 and a lift off process of removing the photoresist PR is performed, a portion of the second metal layer M2 formed on the photoresist PR is removed together with the photoresist PR.

Figure 5C:
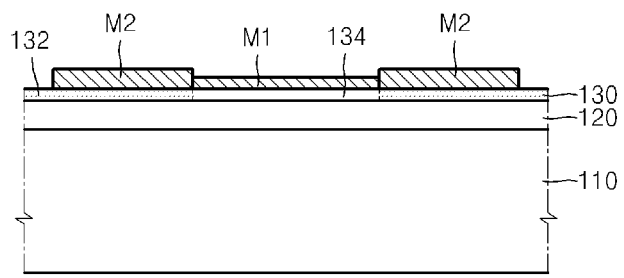
Figure 5D:
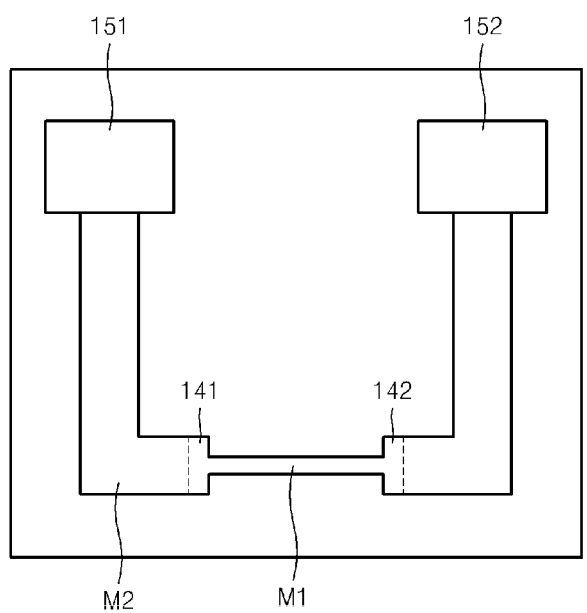
Figure 5E:
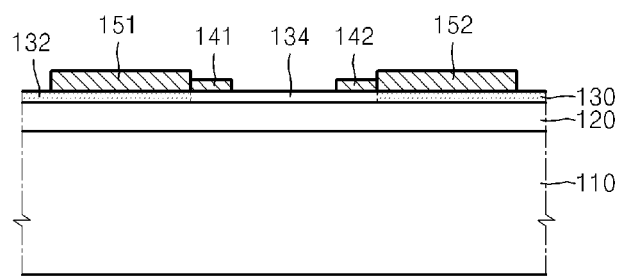

FIGS. 5C and 5D are a cross-sectional view and a plan view, respectively, after the lift off process has been performed. Referring to FIGS. 5C and 5D, a first electrode 141, a second electrode 142, and a first electrode pad 151 and a second electrode pad 152 which will be connected to the first electrode 141 and the second electrode 142, respectively, are formed. Next, when a portion of the first metal layer M1 formed on the nanoelectrode region 134 of the graphene sheet 130 is etched, the nanoelectrode region 134 is exposed, and an electrode structure including the first electrode 141, the first electrode pad 151, the second electrode 142, and the second electrode pad 152, which are connected to both ends of the nanoelectrode region 134, respectively, is completed, as illustrated in FIG. 5E.

Figure 5F:
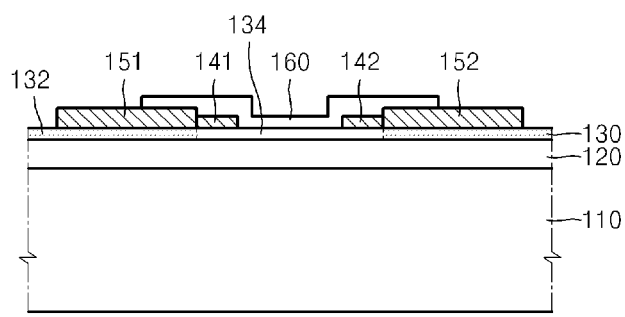

Next, as shown in FIG. 5F, a passivation layer 160 is formed above the electrode structure. In this case, the first electrode pad 151 and the second electrode pad 152 are exposed. The passivation layer 160 may be formed of $Al_2O_3$, for example.

Figure 5G:
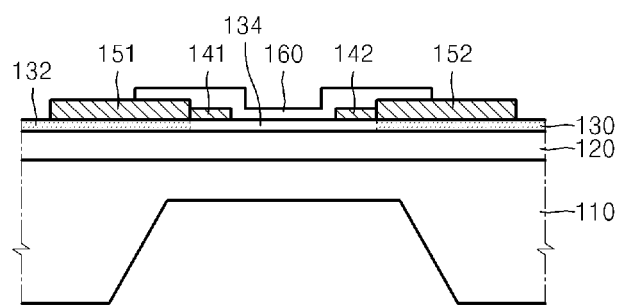
Figure 5H:
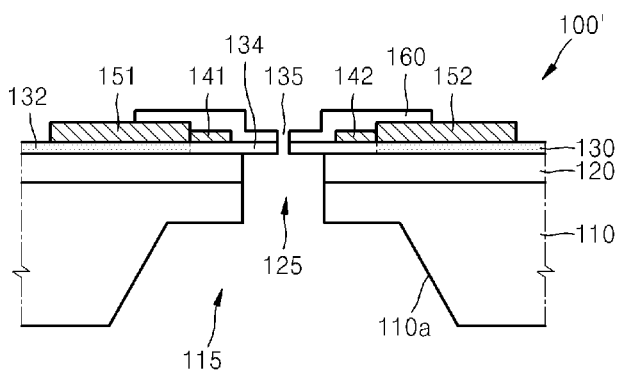

FIGS. 5G and 5H illustrate a process of forming the opening 115 (i.e., FIG. 5G) and the micropore 125 and the nanogap 135 (i.e., FIG. 5H). First, after the opening 115 has been formed in the bottom surface of the substrate 110 by using a method, such as, for example, etching or the like, the micropore 125 may be formed in a position in which the micropore 125 is connected to the opening 115, by using FIB equipment. In addition, the nanogap 135 may be formed in a position in which the nanogap 135 is connected to the micropore 125, by using TEM equipment. The micropore 125 may have a larger diameter than that of the nanogap 135 that is, for example, about 100 μm or less, and the nanogap 135 may be have a diameter of, for example, about 50 nm or less. The shape of the nanogap 135 is not limited thereto, and the nanogap 135 may have a circular shape, an oval shape, or a polygonal shape, for example. A nanogap sensor 100' is manufactured by performing the above processes.

As described above, according to the one or more of the above embodiments of the disclosure, a nanogap sensor is a structure in which a nanoelectrode region having a nanogap of regions of a graphene sheet is electrically activated. The nanogap sensor may implement a nanoelectrode having a nanosize in an electric aspect by using an electrode material formed to have a larger size than a nanosize in a physical aspect.

In addition, since the nanogap is implemented using the graphene sheet, the length of the nanogap through which target biomolecules pass is very small so that resolution of target molecules detection may be improved, compared to conventional techniques.

In addition, since the micropore that faces the nanogap is formed to have a larger size than a nano size and, for example, about micron size, a process of manufacturing the nanogap sensor may be easily performed, and a process of aligning the micropore and the nanogap is not necessary.

The nanogap sensor and device comprising same, as described herein, can be used for any purpose, but is particularly useful for detecting substances of interest in a sample fluid. Target substances include molecules, especially, biomolecules. The molecule or biomolecule can be any that is capable of passing through the nanogap, such as proteins or nucleic acids (e.g., DNA or RNA). The sample can be any liquid sample capable of containing the target substance of interest, such as water or an electrolyte (buffer) solution, and/or or a biological fluid (e.g., blood, lymph, serum, urine, saliva, etc.).

Thus, provided herein is a method of detecting a biological molecule using the nanogap sensor or device described herein. In one aspect, the method comprises contacting the nanogap sensor with a sample and detecting a change in voltage or a tunneling current between the first and second electrodes, wherein detection of a change in voltage or a tunneling current between the first and second electrodes indicates the presence of a biomolecule in the sample. In another aspect, the method of detecting a biomolecule in a sample comprises introducing a sample into the water tank of the device comprising the nanogap sensor, as described herein; applying a voltage to the third and fourth electrodes, thereby causing any biomolecules contained in the sample to migrate to and through the nanogap sensor; and detecting a change in voltage or a tunneling current between the first and second electrodes, wherein detection of a change of voltage or tunneling current between the first and second electrodes indicates the presence of a biomolecule in the sample.

When the target substance to be detected is a nucleic acid (e.g., DNA or RNA), which comprises individual bases, the bases can be classified (identified or distinguished from one another) based on the change in voltage or change in tunneling current measured as the individual bases of the nucleic acid pass through the nanogap.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nanogap sensor comprising:
    a micropore layer comprising a micropore;
    a graphene sheet disposed on the micropore layer and comprising a nanoelectrode region, wherein the nanoelectrode region comprises a nanogap aligned with the micropore;
    a first electrode disposed on the graphene sheet; and
    a second electrode disposed on the graphene sheet, wherein the first electrode and the second electrode are connected to the nanoelectrode region at opposite ends of the nanoelectrode region relative to the nanogap,
    wherein a region of the graphene sheet other than the nanoelectrode region is an electrically inactive region.

2. The nanogap sensor of claim 1, wherein a surface of the inactive region a fluorine (F)-treated, chlorine (Cl)-treated, or bromine (Br)-treated surface.

3. The nanogap sensor of claim 1, wherein the micropore layer comprises silicon nitride or silicon oxide.

4. The nanogap sensor of claim 1, wherein the graphene sheet has a width of about 100 µm or less.

5. The nanogap sensor of claim 1, wherein the nanoelectrode region has a width of about 100 nm or less.

6. The nanogap sensor of claim 1, wherein the micropore has a diameter that is larger than a diameter of the nanogap.

7. The nanogap sensor of claim 1, wherein the micropore has a diameter of about 100 µm (micrometers) or less.

8. The nanogap sensor of claim 1, wherein the nanogap has a diameter of about 50 nm or less.

9. The nanogap sensor of claim 1, further comprising a substrate having an opening defining a passage from a bottom surface of the substrate to a top surface of the suubstrate, wherein the micropore layer disposed on the top surface of the substrate, and the micropore of the micropore layer is aligned with the opening.

10. The nanogap sensor of claim 9, wherein a side of the opening is inclined such that the opening has a width that decreases from the bottom surface of the substrate towards the top surface of the substrate on which the micropore layer is disposed.

11. A device comprising:
    the nanogap sensor of claim 1 positioned in a water tank for accomodating a sample, wherein the sample contains a biomolecule that can pass through the nanogap of the nanogap sensor; and
    a power supply unit configured to provide an electric field in the water tank such that biomolecules in the sample will move in the water tank.

12. The device of claim 11, wherein the water tank comprises an upper region and lower region relative to the nanogap sensor, and the power supply unit comprises a third electrode and a fourth electrode disposed in the upper and lower regions of the water tank, respectively.

13. The device of claim 11, wherein the water tank is filled with water or an electrolyte solution.

14. A method of manufacturing a nanogap sensor, the method comprising:
    forming a micropore layer on a substrate, wherein the micropore layer comprises an insulating material;
    forming a nanoelectrode on the micropore layer, wherein the nanoelectrode comprises graphene;
    forming a micropore in the micropore layer, wherein the micropore perforates the micropore layer; and
    forming a nanogap in the nanoelectrode, wherein the nanogap perforates the nanoelectrode and is aligned with the micropor,
    wherein forming the nanoelectrode comprises:
        forming a graphene sheet on the micropore layer;
        forming a metal layer on the graphene sheet;
        patterning the metal layer in a structure comprising a nanoregion and a first electrode and a second electrode connected to respective ends of the predetermined nanoregion to expose a portion of the graphene sheet; and
        electrically inactivating the exposed portion of the graphene sheet.

15. The method of claim 14, wherein electrically inactivating the portion of the graphene sheet comprises:
    treating a surface of the portion of the graphene sheet with fluorine (F), chlorine (Cl), or bromine (Br); and
    etching a portion of the nanoregion of the metal layer.

16. The method of claim 15, wherein the metal layer is patterned using electron beam lithography.

17. The method of claim 15, further comprising, before the etching of the portion of the nanoregion of the metal layer, forming a first electrode pad and a second electrode pad connected to the first electrode and the second electrode, respectively.

18. The method of claim 17, wherein the first electrode pad and the second electrode pad are formed using a photolithography process.

19. The method of claim 14, wherein the nanogap is formed using a transmission electron microscope (TEM).

20. A method of detecting a biomolecule in a sample comprising:
   contacting a nanogap sensor of claim 1 with a sample; and
   detecting a change in voltage or a tunneling current between the first and second electrodes;
   wherein detection of a change in voltage or a tunneling current between the first and second electrodes indicates the presence of a biomolecule in the sample.

21. A method of detecting a biomolecule in a sample comprising:
   introducing a sample into the water tank of the device of claim 11;
   applying a voltage to the third and fourth electrodes; and
   detecting a change in voltage or a tunneling current between the first and second electrodes;
   wherein detection of a change in voltage or a tunneling current between the first and second electrodes indicates the presence of a biomolecule in the sample.

22. The method of claim 20, wherein the sample comprises DNA or RNA, and the method further comprises classifying a base of the DNA or RNA based on a change in the tunneling current.

* * * * *